(12) United States Patent
Guillen Garcia et al.

(10) Patent No.: US 9,089,298 B2
(45) Date of Patent: Jul. 28, 2015

(54) CABLE-FREE ARTHROSCOPY

(75) Inventors: Pedro Guillen Garcia, Madrid (ES);
Antonio Lòpez Hidalgo, Madrid (ES);
Marta Guillén Vicente, Madrid (ES);
Jesus López Hidalgo, Madrid (ES);
Miguel Angel López Hidalgo, Madrid (ES); Isabel Guillén Vicente, Madrid (ES)

(73) Assignee: PEDRO GUILLEN GARCIA, Madrid (ES)

( * ) Notice: Subject to any disclaimer, the term of this patent is extended or adjusted under 35 U.S.C. 154(b) by 1065 days.

(21) Appl. No.: 12/008,978

(22) Filed: Jan. 15, 2008

(65) Prior Publication Data

US 2008/0183028 A1 Jul. 31, 2008

Related U.S. Application Data

(60) Provisional application No. 60/911,590, filed on Apr. 13, 2007.

(30) Foreign Application Priority Data

Jan. 19, 2007 (ES) .................................. 200700166

(51) Int. Cl.
*A61B 1/04* (2006.01)
*A61B 1/06* (2006.01)
*A61B 1/317* (2006.01)
*A61B 1/00* (2006.01)

(52) U.S. Cl.
CPC ............. *A61B 1/317* (2013.01); *A61B 1/00105* (2013.01); *A61B 1/041* (2013.01)

(58) Field of Classification Search
CPC ............................. A61B 1/317; A61B 1/00105
USPC .......................... 600/103, 109, 118, 174–176
See application file for complete search history.

(56) References Cited

U.S. PATENT DOCUMENTS

| | | | | |
|---|---|---|---|---|
| 4,633,304 A | * | 12/1986 | Nagasaki | ......................... 348/69 |
| 5,762,629 A | * | 6/1998 | Kambin | ................... 604/164.11 |
| 5,827,172 A | | 10/1998 | Takahashi et al. | |
| 6,007,255 A | * | 12/1999 | Krauter et al. | .................. 385/53 |
| 6,540,668 B1 | | 4/2003 | Schulz et al. | |

(Continued)

FOREIGN PATENT DOCUMENTS

| | | |
|---|---|---|
| DE | 197 42 973 | 4/1998 |
| DE | 198 59 155 | 7/2000 |

(Continued)

OTHER PUBLICATIONS

JPO computer English translation of JP 2005-342400 dated Dec. 15, 2005.

(Continued)

*Primary Examiner* — Anhtuan T Nguyen
*Assistant Examiner* — Rynae Boler
(74) *Attorney, Agent, or Firm* — Ladas & Parry LLP

(57) ABSTRACT

The present invention relates to an arthroscopy apparatus, comprising at least three elements selected from: a conventional arthroscopic lens (12), to which there is coupled a power supply device or capsule, in the inside of which is the power source (1), and a miniature camera (8), characterized by not comprising connecting cables.

20 Claims, 2 Drawing Sheets

(56) References Cited

U.S. PATENT DOCUMENTS

| | | | |
|---|---|---|---|
| 6,572,536 B1 * | 6/2003 | Bon et al. | 600/133 |
| 2001/0015754 A1 * | 8/2001 | Nakashima et al. | 348/65 |
| 2001/0015756 A1 | 8/2001 | Wilcock et al. | |
| 2002/0022763 A1 * | 2/2002 | Sano et al. | 600/109 |
| 2004/0236180 A1 * | 11/2004 | Uchiyama et al. | 600/109 |
| 2005/0261554 A1 | 11/2005 | Scholly | |
| 2007/0129602 A1 * | 6/2007 | Bettesh et al. | 600/118 |

FOREIGN PATENT DOCUMENTS

| | | |
|---|---|---|
| DE | 198 59 155 A1 | 7/2000 |
| DE | 100 56 438 | 5/2002 |
| JP | 2001-231739 A | 8/2001 |
| JP | 2001-251611 | 9/2001 |
| JP | 2001-251612 | 9/2001 |
| JP | 2001251612 A * | 9/2001 |
| JP | 2003-198894 A | 7/2003 |
| JP | 2003-250758 | 9/2003 |
| JP | 2005-342034 | 12/2005 |
| JP | 2005-342400 | 12/2005 |
| JP | 2006-109851 A | 4/2006 |

OTHER PUBLICATIONS

JPO computer English translation of JP 2001-251612 dated Sep. 14, 2001.
JPO computer English translation of JP 2005-342034 dated Dec. 15, 2005.
English abstract of DE 10056438 dated May 23, 2002.
English abstract of JP 2001-251611 dated Sep. 14, 2001.
English abstract of JP 2001-251612 dated Sep. 14, 2001.
English abstract of JP 2003-250758 dated Sep. 9, 2003.
English abstract of JP 2005-342400 dated Dec. 15, 2005.

* cited by examiner

CABLE-FREE ARTHROSCOPY

This application claims the benefit of U.S. Provisional Applications No. 60/911,590 filed Apr. 13, 2007 and incorporates the same by reference.

FIELD OF THE INVENTION

The present invention is related to traumatology, a medical specialty dedicated to the diagnosis and treatment of trauma injuries that particularly affect the locomotor system. The invention specifically describes a cable-free apparatus or system which can be used in any type of minimally invasive surgery or arthroscopy, particularly in arthroscopic surgical observations and procedures.

BACKGROUND OF THE INVENTION

Arthroscopy was invented by the Japanese doctor from the University of Tokyo, K. Takayi (1918), using a cystoscope with which he observed the inside of the knee. The first arthroscopic examination was carried out in a cadaver knee in Japan in 1938. Doctor M. Watanabe subsequently succeeded Doctor K. Takayi and persisted in his labor for developing the arthroscopic technique whereby in 1960, in collaboration with Dr. S. Takeda, he presented the arthroscope 21, designed for the arthroscopy of the knee joint. In 1962 Doctor Watanabe was the first to carry out a meniscectomy of the PHMM (posterior horn of the medial meniscus) by arthroscopy.

In 1966, Doctor R. W. Jakson removed two free bodies from the knee and in 1970, a bucket handle using the arthroscopic technique. Doctor R. W. Jakson traveled to Japan, and surprised and fascinated by the viewing of the knee joint carried out by Watanabe, on his return to Toronto he developed arthroscopy and positively influenced the establishment of said technique in the Western world. Doctor R. W. Jakson was thus the person responsible for this progress, although many authors had an influence in the imposition of arthroscopy in the 70s such as: Dandy, 1978; Carson, 1979; Eikelara, 1975; Ikeuchi, 1979; OR'Connor, 1979 or Guillen, 1979.

In the 70s, in first generation arthroscopy, the inside of a joint was viewed with direct viewing through a lens which was fed with a cold-light source and cable. There were teaching optics for taking photographs and for the collaborator to look at the surgeon who is operating at that time.

In the 80s, second generation arthroscopy was developed and arthroscopic cameras appeared which displayed the image of the inside of the joint on a screen, after being perfectly adapted to the lens. This second step in arthroscopy requires two cables crossing the surgical field and requiring disinfection because they are contamination and infection sources. The lens, through a connection with the cable to the light source, receives the illumination which it transfers to the joint, which is full of serum and is thus made visible. The illumination system comprises a light source, generally xenon or tungsten, with an adjustable intensity according to the articular tissue which is to be focused on, and a glass fiber cable connected to the arthroscope. Said cable, with a length of about two meters, crosses the entire operating field, becoming a contamination source, causing post-arthroscopic septic arthritis. Said cable must therefore be sterilized prior to any operation. The deterioration of the glass fibers further negatively affects the desirable aseptic conditions which must be maintained in the operating room.

The inside of the joint is visually inspected with the lens illuminating the joint which is full of serum. After the direct viewing, a lens articulated with a photographic camera is applied to obtain photos. This methodology is known as diagnostic arthroscopy.

The camera applied to the lens and connected by a long cable with an extension of two to three meters, sterilized or in a sterile cover, to a monitor has formed a great advance in second generation arthroscopy. Operations are thus recorded or photographed, facilitating the knowledge and teaching of advanced surgical procedures.

However, the second generation arthroscopic techniques that are currently used have obligations which are responsible for most of the articular infections that the patient suffers from when he or she is subjected to an operation in which said arthroscopic techniques are used. A review of the medical literature from 1988 to 2005 was carried out in the present invention. Said study shows different percentages of infection in arthroscopic surgery which vary from 0.4 to 2.0%, this figure being greater in the shoulder than in the knee. This percentage of infection decreases when arthroscopies are carried out using the apparatus of the invention.

The present invention therefore relates to an apparatus or system (hereinafter apparatus of the invention) for carrying out arthroscopies which does not comprise cables or a connection joining it to the arthroscopy tower, preventing the articular infections caused by said cables and referred to previously. The present invention therefore forms the step from second generation arthroscopy (comprising arthroscopic cameras taking images of the inside of the joint and showing them on a screen after being perfectly adapted to the lens, requiring two cables crossing the surgical field and requiring being disinfected since they are contamination and infection sources) to third generation arthroscopy, which is the object of the present invention and enables carrying out arthroscopies without cold-light cables, decreasing the risk of patients suffering from articular infections.

On the other hand, apart from providing the surgeon with the possibility of carrying out risk-free arthroscopies or arthroscopies with a lower risk of articular infection and therefore enabling the patient to undergo an operation with a lower risk of infection, the apparatus of the invention, due to the fact that it does not comprise cables, is a surgical tool which can be used by the arthroscopist more independently than those existing in the state of the art, which comprise cables.

Since it does not comprise cables or connection, the apparatus of the invention, further involves a simplification of the system used in the state of the art, which fact provides it with the possibility of being used in medical offices, without requiring the complex installations (generally in operating rooms with stricter and more expensive asepsis and sterility conditions) associated to current arthroscopy systems. The possibility of being used without having to use complex installations has the advantage that the economic cost associated to said use of the service is reduced.

The portability of the system of the invention, which makes it more suitable for ambulatory diagnosis and surgery in places far from the large hospital centers, is also emphasized.

DESCRIPTION OF THE INVENTION

Brief Description of the Invention

The present invention relates to an apparatus or system for carrying out arthroscopies which does not comprise cables or connection joining it to the arthroscopy tower, which prevents or decreases the risk of the patient contracting articular infections caused by said cables, the use of which is easier than that of the apparatuses existing in the state of the art (which comprise cables) and reduces the complexity and economic cost of the installations associated to its use.

As mentioned in the present invention, the arthroscopy tower relates to a trolley with wheels formed by several stories where a TV screen, the video center, the cold-light source and the power source for motors or any other apparatus for the same use are housed.

Apart from preventing or reducing the articular infections in patients who are surgically treated with the apparatus or system of the invention, as a result of the fact that the latter does not comprise cables or wired light source, the latter has another series of advantages with respect to the systems existing in the state of the art, enabling its use to be more comfortable and effective: it does not require an arthroscopy tower, it does not require the cable of the video camera connected to the arthroscopy tower, it has a lower apparatus and cable obligation, disappearance of the disinfection bins for cold-light cables and lower cost.

DETAILED DESCRIPTION OF THE INVENTION

The present invention relates to an apparatus or system for carrying out arthroscopies which does not comprise cables or connection joining it to the arthroscopy tower, which prevents or decreases the risk of the patient contracting articular infections caused by said cables, the use of which is easier than that of the apparatuses existing in the state of the art (which comprise cables) and reduces the complexity and economic cost of the installations associated to its use.

Figure 1:
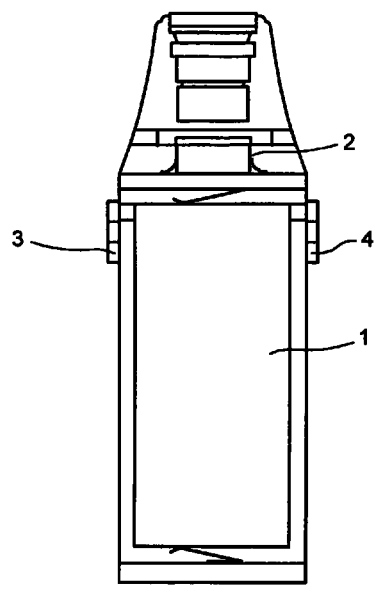
FIG. 1 shows the disposable or reusable cable-free, cold-light energy device or capsule internally containing:
1. The battery.
2. Led-diode and light intensity control.
3. (−) Push-button, light intensity decrease regulator.
4. (+) Push-button, light intensity increase regulator.

Since it does not comprise cables, the lens of the apparatus of the invention has attached a power supply device or capsule (FIG. 1). Said device or capsule, which is disposable, allows adjusting the applied energy by means of a battery (1) with a variable duration and size, a light intensity control and a led-diode (2) which by means of a universal adaptor enables its application to any arthroscopic lens, being able to be used attached to other illumination systems: a frontal illumination system such as the photophore, a fixed base illumination system, etc. Said led-diode control is operated by means of respective push-buttons (3 and 4). The power supply device shown (FIG. 1) also allows rotating the lens (12).

On the other hand, the arthroscopic camera (FIG. 2) does not require cable either and has a central keyboard to switch the monitor or computer on and take photos or videos which can be filed in the clinical records.

In a preferred embodiment of the invention, the power supply device is integrated in the camera-carrying device itself and/or in the lens-carrying device.

In another preferred embodiment of the invention, the energy device or capsule (FIG. 1), or the miniature camera (FIG. 2), characterized by the fact that they do not comprise connecting cables, can be coupled to any surgical apparatus or system needing a power or light source.

Figure 2:
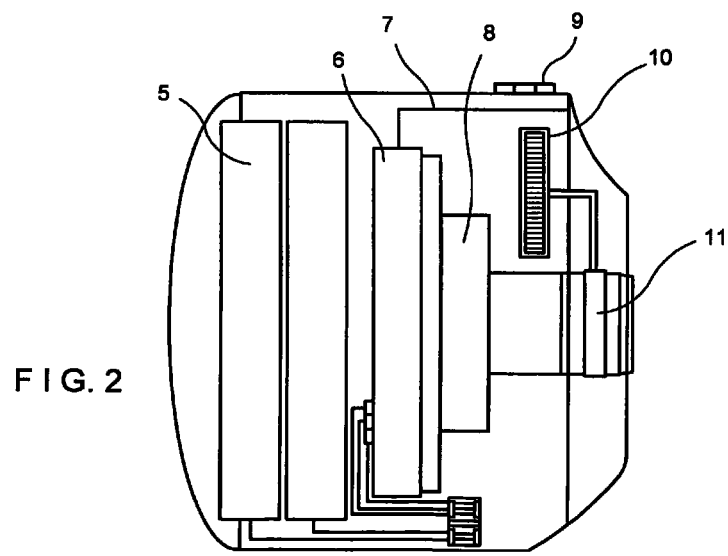
FIG. 2 shows a cable-free miniature camera offering the possibility of recording video and/or photographs as well as focus control. The camera is comprised by:
5. Batteries.
6. Emitter.
7. Antenna.
8. Video or photographic camera.
9. On switch.
10. Focus.
11. Objective (25 mm).

The apparatus of the invention (FIG. 3) therefore comprises a conventional arthroscopic lens to which the two elements shown and described in FIGS. 1 and 2 are coupled. The arthroscopy apparatus or system thus comprises:

A conventional lens (8) with any angling (0°, 30°, 70° or greater), for example 30° and 4 mm, to which there is coupled a power supply device or capsule carrying at least one cell or battery with a variable duration and size, with energy for different durations, and being disposable or not. This capsule generates light, which can be regulated and said capsule can further rotate the lens (FIG. 1). The energy capsule can be attached to a light device (frontal light or photophore in neurosurgery, ear, nose, throat, urology, etc).

Figure 3:
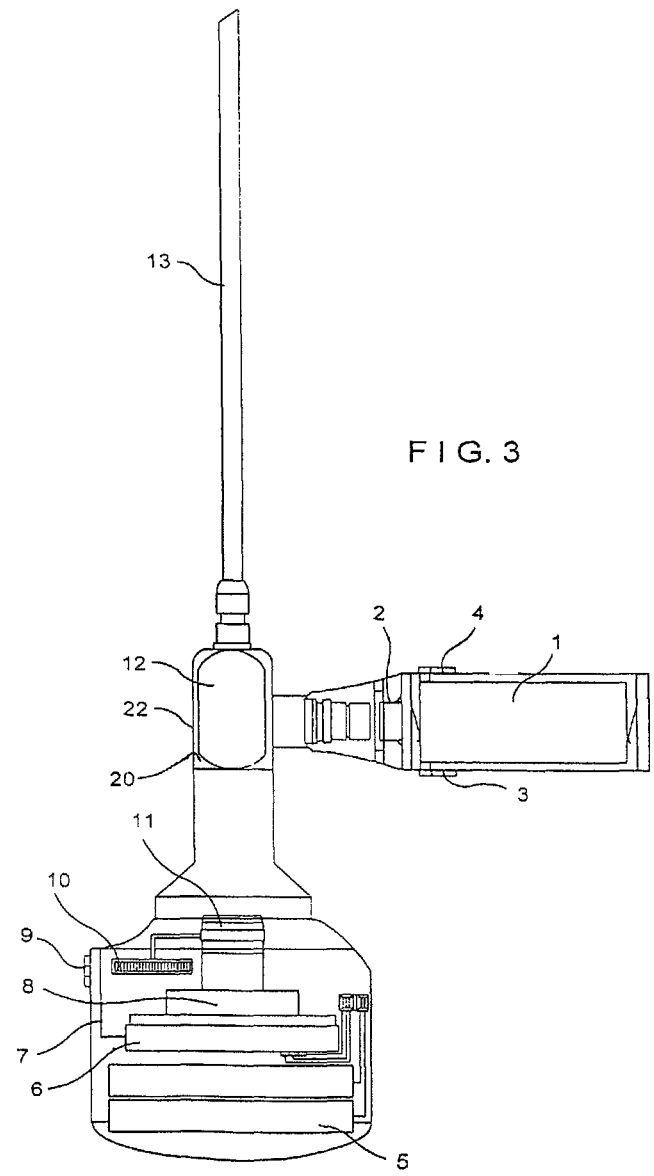
FIG. 3 shows a conventional arthroscopic lens to which the two elements shown in FIGS. 1 and 2 are coupled. The arthroscopic lens resulting from said coupling is thus comprised by:
1. Battery.
2. Led-diode (light intensity control).
3. (−) Push-button, light decrease regulation.
4. (+) Push-button, light increase regulation.
5. Batteries
6. Emitter.
7. Antenna.
8. Miniaturized video or photographic camera.
9. Switch.
10. Focus.
11. Objective (25 mm).
12. Arthroscopic lens.
13. Needle/catheter/arthroscopic tube.

A conventional sheath 22 covering and protecting the lens is shown in FIG. 3. The sheath is used as a way to protect the lens, prevent it from breaking. Furthermore, since it has a diameter greater than the lens, the sheath causes the formation of a cavity 20 in which serum facilitating the viewing upon carrying out arthroscopies circulates.

A miniature video camera (8) with an antenna (7) and switches (9) for switching the monitor on and carrying out recordings or taking photographs (FIG. 2).

Therefore, in a first aspect, the present invention relates to a system or apparatus comprising a conventional arthroscopic lens (12) to which there is coupled a device or capsule in the inside of which is a power supply or source (1) and a miniature camera (8), characterized by not comprising connecting cables for the connection to the power source.

A second aspect of the present invention relates to a power supply device or capsule (1) characterized by not comprising connecting cables for the connection to the power source, to be coupled to a conventional arthroscopic lens.

A third aspect of the present invention relates to a miniature camera (8), preferably with a weight of less than 10 grams, characterized by not comprising connecting cables for the connection to the power source, to be coupled to a conventional arthroscopic lens.

A fourth aspect of the present invention relates to the use of a system or apparatus comprising a conventional arthroscopic lens (12) to which there is coupled a power supply device or capsule, in the inside of which is the power source (1) and a miniature camera (8), characterized by not comprising connecting cables for the connection to the power source, for carrying out arthroscopies, where the arthroscopies are simple arthroscopies, diagnostic arthroscopies or minimally invasive surgical arthroscopies or for carrying out arthroscopies intended for studying natural body cavities such as those of the digestive, pulmonary or urogenital system or for carrying out arthroscopies intended for the surgical treatment of organ and tissue injuries and particularly those injuries affecting joints and brain ventricles, in humans or animals.

A fifth aspect of the present invention relates to the use of the power supply device or capsule in the inside of which is the power source (1) characterized by not comprising connecting cables to said power source (1), to be coupled to a conventional arthroscopic lens (12) and/or to the miniature camera (FIG. 2), for manufacturing apparatuses or systems which can be used in surgery and characterized by not comprising cables and needing a power or light source, where the surgery apparatus or system is specifically a cable-free arthroscopy apparatus.

The sixth aspect of the present invention relates to the use of the miniature camera (8) characterized by not comprising connecting cables for the connection to the power source (1), for manufacturing apparatuses or systems which can be used in surgery and characterized by not comprising cables and needing a power or light source, where the surgery apparatus or system is specifically a cable-free arthroscopy apparatus.

The last aspect of the present invention relates to a method for carrying out arthroscopies (hereinafter method of the invention), in humans and animals, characterized by using an arthroscopy apparatus comprising at least three elements selected from: a conventional arthroscopic lens (12), to which there is coupled a power supply device or capsule, in the inside of which is the power source (1) and a miniature camera (8), characterized by not comprising connecting cables. The method of the invention is also characterized in that the power supply device or capsule, in the inside of which is the power source (1), to be coupled to the conventional arthroscopic lens (12), does not comprise connecting cables. The method of the invention is further also characterized in that the miniature camera or the video camera or the photographic camera, to be coupled to the conventional arthroscopic lens, do not comprise connecting cables. The arthroscopies carried out by the method of the invention are comprised in the following group: simple arthroscopies, diagnostic arthroscopies, minimally invasive surgical arthroscopies, arthroscopies for studying natural body cavities such as those of the digestive, pulmonary or urogenital system, arthroscopies intended for the surgical treatment of organ and tissue injuries and particularly those injuries affecting joints and brain ventricles.

The system or apparatus of the invention has been used in phantoms (arthroscopy workshops with knee reproductions for example) and cadavers, where it has been shown to be useful, easy and safe. It has further been tested in medical offices showing the advantages it involves and which have already been described: speeding up surgery, lower economic cost and less suffering for the patient since the risk of infection decreases.

The invention claimed is:
1. The arthroscopy apparatus comprising:
 (a) an arthroscopic lens;
 (b) an arthroscopic tube comprising a first end and a second end, an elongate portion at the first end and a cavity portion disposed between the elongate portion and the second end, the cavity portion being wider than the elongate portion and housing the arthroscopic lens, the cavity portion being formed by a sheath that covers and protects the arthroscopic lens while still providing for a space around the arthroscopic lens;
 (c) a power supply module detachably coupled to the cavity portion of the arthroscopic tube, the power supply module comprising a power source and a light source; and
 (d) a camera module for coupling to the second end of the arthroscopic tube, the camera module comprising a cable-free miniature camera;
wherein the arthroscopic lens is rotatable with respect to the sheath with the light source coupled to the cavity portion; and wherein the camera module has its own battery and is not connected to the power source in the power supply module by cable.

2. The arthroscopy apparatus according to claim 1, wherein the power supply module comprises a universal adapter that enables the power supply module to be detached from the cavity portion of the arthroscopy apparatus and connected to another apparatus.

3. The arthroscopy apparatus according to claim 2, wherein the camera module can be coupled either to the arthroscopic tube or to another apparatus.

4. The arthroscopy apparatus according to claim 3, wherein the camera module is coupled to the arthroscopic tube.

5. The arthroscopy apparatus according to claim 1, wherein the camera module can be coupled either to the arthroscopic tube or to another apparatus.

6. The arthroscopy apparatus according to claim 5, wherein the camera module is coupled to the arthroscopic tube.

7. The arthroscopy apparatus according to claim 1, wherein the miniature camera is a video camera.

8. The arthroscopy apparatus according to claim 1, wherein the miniature camera is a photographic camera.

9. A method for carrying out an arthroscopy procedure in a human or animal, comprising the steps of:
 providing an arthroscopy apparatus according to claim 1, and
 inserting the arthroscopy apparatus into the human or animal.

10. The method according to claim 9, wherein the step of inserting includes inserting the arthroscopy apparatus into a digestive system of the human or animal.

11. The method according to claim 9, wherein the step of inserting includes inserting the arthroscopy apparatus into a pulmonary or urogenital system of the human or animal.

12. The arthroscopy apparatus according to claim 1, wherein the power supply module is coupled to the arthroscopic lens so as to allow a rotational movement of the lens.

13. The arthroscopy apparatus according to claim 1, wherein the power supply module is disposable.

14. The arthroscopy apparatus according to claim 1, further comprising a wireless transmitter for wirelessly transmitting an image captured by the miniature camera to a display.

15. The arthroscopy apparatus according to claim 1, wherein the miniature camera is arranged to capture an image from the arthroscopic lens.

16. The arthroscopy apparatus according to claim 1, wherein the power supply module includes a regulator for controlling a light intensity of the light source.

17. The arthroscopy apparatus comprising:
 (a) an arthroscopic lens;
 (b) an arthroscopic tube having a first end and a second end and comprising (i) an elongate portion at the first end and (ii) means for defining a cavity portion that is wider than the elongate portion between the elongate portion and the second end and for forming a sheath for the arthroscopic lens that provides a space around the arthroscopic lens while protecting the arthroscopic lens from breaking;
(c) a power supply module detachably coupled to the cavity means, the power supply module comprising a power source and a light source; and
(d) a camera module for coupling to the second end of the arthroscopic tube, the camera module comprising a cable-free miniature camera;

wherein the arthroscopic lens is rotatable with respect to the sheath with the light source coupled to the cavity portion; and
wherein the camera module has its own battery and is not connected to the power source in the power supply module by cable.

18. The arthroscopy apparatus according to claim 17, wherein the arthroscopy lens is angled at an angle of 30° or greater.

19. The arthroscopy apparatus comprising three independent elements:
(a) an arthroscopy lens (12);
(b) a supply device or capsule (1) having a light source in an interior thereof; and
(c) a miniaturized camera (18) that does not require a cable and is configured to produce photographs or videos, the miniaturized camera comprising a battery (5), an emitter (6), an antenna (7), an on/off switch (9), a focus (10) and an objective (11);

wherein the elements are configured so that light can enter directly from the light source of the supply device or capsule (1) into the arthroscopy lens (12) and there can be a coupling of the light source to the arthroscopy lens (12);
wherein the apparatus further comprises a sheath covering and protecting the arthroscopy lens (12), the sheath having a diameter greater than a diameter of the arthroscopy lens; and
wherein the coupling of the light source to the arthroscopy lens (12) permits rotation of the arthroscopy lens (12) with respect to the sheath.

20. The arthroscopy apparatus according to claim 19, wherein the supply device or capsule having the light source in the interior thereof comprises the battery (5), an LED diode and a light intensity control (2), and two pushbuttons regulating decrease (3) and increase (4) in light intensity.

* * * * *